United States Patent [19]

Graboyes et al.

[11] 4,374,252

[45] Feb. 15, 1983

[54] BENZYL 5-METHYL-4-IMIDAZOLECARBOXYLATE

[75] Inventors: Harold Graboyes, Philadelphia; Thomas J. Kasper, Media; Praful D. Vaidya, Warminster, all of Pa.

[73] Assignee: SK&F Lab Co., Carolina, P.R.

[21] Appl. No.: 329,164

[22] Filed: Dec. 10, 1981

Related U.S. Application Data

[62] Division of Ser. No. 195,278, Oct. 8, 1980, Pat. No. 4,328,349.

[51] Int. Cl.³ ............................................ C07D 233/90
[52] U.S. Cl. ..................................................... 548/343
[58] Field of Search ........................................ 548/343

[56] References Cited

U.S. PATENT DOCUMENTS 3,715,365  2/1973  Schulze ................................ 548/335
3,950,333  4/1976  Durant et al. ....................... 544/224
4,134,983  1/1979  Baldwin ............................... 548/343
4,146,724  3/1979  Friederang et al. ................. 548/343

FOREIGN PATENT DOCUMENTS 1341375  12/1973  United Kingdom ................ 548/335

OTHER PUBLICATIONS

Bohme et al., Chemische Berichte 91: 988–996 1958.
Ertel et al., Liebigs Ann. Chem. 1399–1406 1974.

Primary Examiner—Jane T. Fan
Attorney, Agent, or Firm—Joan S. Keps; Richard D. Foggio; Alan D. Lourie

[57] ABSTRACT

A process for the preparation of 5-methyl-4-imidazolecarboxylic acid esters from acetoacetic acid esters. The products of this process are useful as intermediates for preparing cimetidine.

1 Claim, No Drawings

BENZYL 5-METHYL-4-IMIDAZOLECARBOXYLATE

This is a division of application Ser. No. 195,278 filed Oct. 8, 1980 now U.S. Pat. No. 4,328,349 issued May 4, 1982.

This invention relates to a process for preparing 5-methyl-4-imidazolecarboxylic acid esters from acetoacetic acid esters. The 5-methyl-4-imidazolecarboxylic acid esters which are the products of this process are useful as intermediates for preparing histamine $H_2$-antagonists, for example cimetidine.

Cimetidine, which is N-cyano-N'-methyl-N''-[2-(5-methyl-4-imidazolylmethylthio)ethyl]guanidine, is a histamine $H_2$-receptor blocking agent of value as an inhibitor of gastric acid secretion. Cimetidine is widely used in the treatment of duodenal ulcers.

This invention also relates to a new compound prepared by the process of this invention, that is benzyl 5-methyl-4-imidazolecarboxylic acid ester.

Methods of preparing esters of 5-methyl-4-imidazolecarboxylic acids have been described. Bohme et al., in *Chemische Berichte* 91:988–996 (1958), described the preparation of ethyl 5-methyl-4-imidazolecaboxylate by the reaction of the ethyl ester of α-hydroxyacetoacetic acid with formamide and also by the reaction of ethyl α-chloroacetoacetate with formamide and water. The preparation of the corresponding isopropyl ester by reacting isopropyl chloroacetoacetate with formamide and water in the presence of formic acid is disclosed in U.S. Pat. No. 4,146,724.

Durant et al., in U.S. Pat. No. 3,950,333, described the preparation of 4-substituted-5-imidazolecarboxylic acid ethyl esters by reaction of an ethyl alkanoylacetate with sodium nitrite, reduction of the resulting ethyl 2-hydroxyimino-3-oxoalkanoate to give the 2-amino-3-oxo compounds and treatment of that compound with formamide.

Ertel et al., *Liebigs Ann. Chem.* 1399 (1974), reported the preparation of 1-hydroxy-imidazoles by the reaction of a 2-hydroxyiminoacetoacetate with an aldehyde and ammonia.

According to the process of the present invention, 5-methyl-4-imidazolecarboxylic acid esters are prepared by the following procedure:

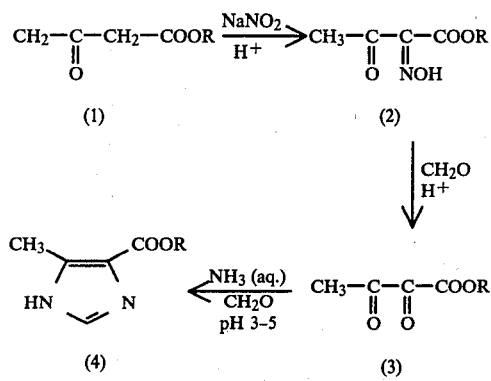

in which R is lower alkyl having 1–4 carbon atoms or benzyl.

Preferably, the process of this invention is carried out without isolating the two intermediates, i.e. (2) and (3) above. Thus, the preferred process may be represented as follows:

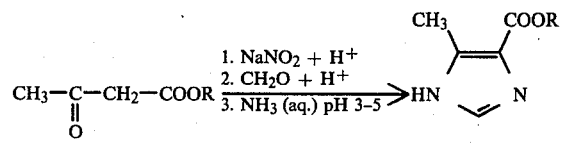

In the first step of the process of this invention, a lower alkyl ester of acetoacetic acid is reacted with nitrous acid. The nitrous acid is preferably generated by reacting sodium nitrite with an acid, preferably acetic acid. This reaction is preferably carried out at reduced temperature, for example at about 0°–15° C., for about 3–6 hours. If isolation of the hydroxyimino intermediate (2) is desired, ethyl acetate is the preferred solvent.

Thereafter, either with or without isolating the hydroxyimino intermediate (2), that intermediate is reacted with formaldehyde and a mineral acid for example hydrochloric acid, sulfuric acid or phosphoric acid, preferably hydrochloric acid. It is preferable to add the hydroxyimino compound to the formaldehyde/acid solution, rather than to add the formaldehyde/acid to the hydroxyimino compound, in order to better control the exothermic reaction temperature. In carrying out the reaction in a single vessel, it is preferable to add formaldehyde to the hydroxyimino compound to form a suspension and then add the acid to the suspension. This reaction to form the diketo compound is preferably carried out at about 0°–15° C. The resulting mixture containing the diketo compound, i.e. α,β-dioxobutyric acid ester, and formaldehyde is treated with aqueous ammonia to raise the pH to about 3 to 5. The reaction mixture is held at about 65°–70° C. for about 30–60 minutes, then ammonia is added to neutralize the reaction mixture (pH 7). Cooling and filtering gives the 5-methyl-4-imidazolecarboxylic acid ester.

Good yields of the product are obtained by the process of this invention, particularly when the acetoacetate ester used is the ethyl ester and when the mineral acid used is hydrochloric acid.

The process is quite acceptable environmentally, that is, no extensive treatment of the effluent is needed to meet environmental requirements.

The 5-methyl-4-imidazolecarboxylic acid esters prepared by the process of this invention may be used to prepare histamine $H_2$-antagonists, in particular cimetidine, by reducing the ester to give the 5-methyl-4-hydroxymethylimidazole, reacting the hydroxymethyl compound with cysteamine and then reacting the resulting 5-methyl-4-[(2-aminoethyl)thiomethyl]imidazole with dimethyl-N-cyanoimidodithiocarbonate and reacting the resulting N-cyano-N'-[2-((5-methyl-4-imidazolyl)methylthio)ethyl]-S-methylisothiourea with methylamine. These processes are described in U.S. Pat. No. 3,950,333. A process for reducing the ester to the hydroxymethyl compound using alkali metal or calcium in liquid ammonia is described in U.S. Pat. No. 4,063,023.

The invention is illustrated by the following examples. The temperatures indicated therein are °C.

EXAMPLE 1

To a cold (5°) stirred mixture of 3.9 kg. of ethyl acetoacetate in 2.25 liters of glacial acetic acid was added a solution of 2.25 kg. of sodium nitrite in 3 liters of water over one hour at 0°–15°. The reaction mixture was stirred at 0°–15° for six hours and worked up to give ethyl 2-hydroxyimino-acetoacetate (4.57 kg.) in 96% yield.

To a cool (0°–5°) stirred suspension of 53 g. (1.76 m.) of paraformaldehyde in 172 ml. (2 m.) of 37% hydrochloric acid and 40 ml. of water was added 79.5 g. (0.5 m.) of ethyl 2-hydroxyimino-acetoacetate over 20 minutes at 0°–10°. The mixture was stirred for four hours at 0°–5°, then 200 ml. of aqueous ammonia (28%) was added over 20 minutes until pH reached 4–5 and the temperature rose to 70°. The reaction mixture was held at 60°–70° for 30 minutes and then 60 ml. of aqueous ammonia (28%) was added to pH 7 at 65°–70°. The mixture was cooled to 10°, then the product was filtered off and washed with water and isopropanol and dried to give 56 g. (72.7% yield) of ethyl 5-methyl-4-imidazolecarboxylate, m.p. 203°–205°, assay 98–100%.

EXAMPLE 2

To a cold (5°) stirred solution of 130 g. (1 m.) of ethyl acetoacetate in 75 ml. (1.3 m.) of glacial acetic acid was added 76 g. (1 m.) of sodium nitrite in 110 ml. of water over one hour at 0°–15°. The reaction mixture was stirred for 3–6 hours a 0°–15°. Paraformaldehyde (105 g., 3.5 m.) was added over 10 minutes to the reaction mixture at 0° followed by 517 ml. (6 m.) of concentrated hydrochloric acid added slowly over one hour maintaining the exothermic reaction temperature at 0°–10° by external cooling. After 3.5 hours of stirring at 0°–10°, 650 ml. of aqueous ammonia (28%) was added over 20 minutes and the temperature was allowed to rise to 70° with pH at 5. The reaction mixture was held at 65°–70° at pH 5 for 30 minutes and then 65 ml. of aqueous ammonia (28%) was added until the mixture was neutral. The reaction mixture was cooled to 10° and the solid was filtered off, washed with water and isopropanol and dried to give ethyl 5-methyl-4-imidazolecarboxylate (108.5 g., yield 70.4%). Assay: 98.4%.

EXAMPLE 3

To a stirred cold (0°) suspension of concentrated hydrochloric acid (516 ml.) and paraformaldehyde (105 g.) was added ethyl 2-hydroxyiminoacetoacetate prepared from 130 g. (1 m.) of ethyl acetoacetate over two hours maintaining the reaction temperature at 5°–15°. After stirring one hour at 5°–15°, aqueous ammonia (28%) was added slowly until pH reached 5 and temperature rose to 70° over 35 minutes. The reaction mixture was held at pH 5 at 65°–70° for 30 minutes and then aqueous ammonia (28%) was added until the mixture was neutral. The mixture was cooled to 10° and the solid material was filtered off and washed with water and isopropanol and dried to give ethyl 5-methyl-4-imidazolecarboxylate, m.p. 204°–206°, yield 61–65%.

EXAMPLE 4

One mole of ethyl 2-hydroxyimino-acetoacetate, prepared from 130 g. (1 m.) of ethyl acetoacetate, was added over 75 minutes to a stirred suspension of 166 ml. (3 m.) of concentrated sulfuric acid and 105 g. (3.5 m.) of paraformaldehyde at 5°–10°. The mixture was stirred at 5°–10° for four hours and aqueous ammonia (28%) was added to pH 5 and the temperature rose to 70°. The reaction mixture was held for 30 minutes at pH 5 at 65°–70° and then neutralized with aqueous ammonia (28%). The mixture was cooled to 10°. The solid material was filtered off, washed with water and isopropanol and dried to give ethyl 5-methyl-4-imidazolecarboxylate (yield 50%).

Using phosphoric acid in place of sulfuric acid in the above procedure gave ethyl 5-methyl-4-imidazolecarboxylate in 37% yield.

EXAMPLE 5

To a cold (5°) stirred solution of 58.06 g. (0.5 m.) of methyl acetoacetate and 37.5 ml. of glacial acetic acid was added 38 g. (0.55 m.) of sodium nitrite in 55 ml. of water over 30 minutes maintaining the temperature 5°–15°. The reaction mixture was stirred for six hours at 10°. Then, 52.5 g. (1.75 m.) of paraformaldehyde was added. Concentrated hydrochloric acid (259 ml., 3 m.) was added over 45 minutes maintaining the exothermic reaction temperature at 0°–5°. After four hours at 0°–5°, aqueous ammonia (28%) was added to the mixture over 20 minutes to pH 5, temperature 70°. The mixture was stirred at 65°–70°, pH 5 for 30 minutes and then neutralized with aqueous ammonia (28%). The reaction mixture was cooled to 10° and filtered. The solid material obtained was washed with water and isopropanol to give methyl 5-methyl-4-imidazolecarboxylate (36.4 g., 52% yield).

EXAMPLE 6

To a cold (5°) stirred solution of benzyl acetoacetate (1 mole) in glacial acetic acid (75 ml.) was added sodium nitrite solution (1 mole in 110 ml. of water) over one hour at 0°–15°. The resulting suspension was stirred at 10° for three hours and then it was added to a stirring suspension of concentrated hydrochloric acid and paraformaldehyde (3.5 mole) at 5°–15° over 1.5 hours. The exothermic reaction was maintained at 10°–15° by external cooling for 45 minutes. Aqueous ammonia (28%) (525 ml.) was added over 40 minutes to pH 5, temperature 65°–70°. After 30 minutes at 65°–70°, the pH was raised to 6.5 and the reaction mixture cooled to 15°. The aqueous layer was decanted off and the residue was triturated with acetone to give benzyl 5-methyl-4-imidazolecarboxylate, m.p. 203°–205°, 30% yield.

EXAMPLE 7

A 2 liter flask was fitted with an overhead stirrer and a nitrogen inlet and charged with 600 ml. of anhydrous ammonia. A dry-ice acetone cooling bath was provided to aid the collection of ammonia and to cool the reaction. After the ammonia was collected, sodium (33 g., 1.435 m.) was added in portions and dissolved giving a deep blue color. t-Butanol (25 ml., 0.266 m.) was added to this solution. 5-Methyl-4-imidazole-carboxylic acid ethyl ester (50 g., 0.32 m.) was added portionwise. After addition of the ester, the blue solution was stirred for five minutes and methanol (100 ml.) was added dropwise causing the blue color to be discharged after a few ml. had been added. Ammonium chloride (78 g., 1.458 m.) was added in portions. The ammonia was evaporated and isopropanol (700 ml.) was added to the residue and the mixture was refluxed for 30 minutes with vigorous stirring. The mixture was cooled to 40° and acidified (pH about 1) with hydrogen chloride gas. Water (10 ml.) was added and the mixture stirred at 50° for 30 minutes. The mixture was filtered and the filter cake washed with 200 ml. of warm (40°–50°) isopropanol. The solution was concentrated to 100 ml. and diluted with acetone (400 ml.) and ether (100 ml.). The product was collected and dried to give 46.0 g. (96%) of 4-(hydroxymethyl)-5-methylimidazole hydrochloride.

A solution of 4-hydroxymethyl-5-methylimidazole hydrochloride (30.0 g.) and cysteamine hydrochloride (23.0 g.) in acetic acid (200 ml.) was heated under reflux for 10 hours. Following cooling to 15°–20°, the solid which crystallized was collected and washed with isopropyl alcohol to give 4-methyl-5-[(2-aminoethylthiomethyl]-imidazole dihydrochloride, m.p. 189°–192°.

(a) A solution of 4-methyl-5-[(2-aminoethyl)thiomethyl]imidazole (17.0 g.) and N-cyano-N',S-dimethylisothiourea (11.2 g.) in acetonitrile (500 ml.) was heated under reflux for 24 hours. Following concentration, the residue was chromatographed on a column of silica gel with acetonitrile as eluant and the product obtained was finally recrystallized from acetonitrileether to yield N-cyano-N'-methyl-N''-[2-((5-methyl-4-imidazolyl)methylthioethyl]guanidine, m.p. 141°–142°.

(b) A solution of 4-methyl-5-[(2-aminoethyl)thiomethyl]imidazole (23.4 g.) in ethanol was added slowly to a solution of dimethyl-N-cyanoimidodithiocarbonate (20.0 g.) in ethanol, with stirring at room temperature. The mixture was set aside overnight at room temperature. Filtration afforded N-cyano-N'-[2-((5-methyl-4-imidazolyl)methylthio]ethyl]-S-methylisothiourea, m.p. 148°–150°. The filtrate was concentrated under reduced pressure and the mixture was triturated with cold water and the solid obtained, filtered off and recrystallized twice from isopropyl alcohol/ether to yield further product, m.p. 148°–150°.

A solution of methylamine in ethanol (33%, 75 ml.) was added to a solution of N-cyano-N'-[2-((5-methyl-4-imidazolyl)methylthio)ethyl]-S-methylisothiourea (10.1 g.) in ethanol (30 ml.). The reaction mixture was set aside at room temperature for 2.5 hours. Following concentration under reduced pressure, the residue was recrystallized twice from isopropyl alcohol/petroleum ether, affording N-cyano-N'-methyl-N''-[2-((5-methyl-4-imidazolyl)methylthio)ethyl]guanidine, m.p. 141°–143°.

What is claimed is:

1. Benzyl 5-methyl-4-imidazolecarboxylate.

* * * * *

UNITED STATES PATENT AND TRADEMARK OFFICE
CERTIFICATE OF CORRECTION

PATENT NO. : 4,374,252

DATED : February 15, 1983

INVENTOR(S) : Harold Graboyes, Thomas J. Kasper and Praful D. Vaidya

It is certified that error appears in the above—identified patent and that said Letters Patent is hereby corrected as shown below:

Column 1, lines 50-52, structural formula (1) reading $CH_2-\underset{\underset{O}{\|}}{C}-CH_2-COOR$ should read $CH_3-\underset{\underset{O}{\|}}{C}-CH_2-COOR$ Signed and Sealed this Nineteenth Day of April 1983

[SEAL]

Attest:

GERALD J. MOSSINGHOFF

Attesting Officer

Commissioner of Patents and Trademarks